(12) United States Patent
Sage et al.

(10) Patent No.: US 11,655,209 B2
(45) Date of Patent: May 23, 2023

(54) PROCESS FOR SYNTHESIZING AZO COMPOUNDS

(71) Applicant: Arkema France, Colombes (FR)

(72) Inventors: Jean-Marc Sage, Pierre-Benite (FR); Jean-Michel Bossoutrot, Pierre-Benite (FR)

(73) Assignee: Arkema France, Colombes (FR)

( * ) Notice: Subject to any disclaimer, the term of this patent is extended or adjusted under 35 U.S.C. 154(b) by 226 days.

(21) Appl. No.: 16/979,582

(22) PCT Filed: Mar. 14, 2019

(86) PCT No.: PCT/FR2019/050565
§ 371 (c)(1),
(2) Date: Sep. 10, 2020

(87) PCT Pub. No.: WO2019/175510
PCT Pub. Date: Sep. 19, 2019

(65) Prior Publication Data
US 2020/0407312 A1     Dec. 31, 2020

(30) Foreign Application Priority Data
Mar. 16, 2018   (FR) ..................... 1852264

(51) Int. Cl.
| | | |
|---|---|---|
| *C07C 253/30* | (2006.01) | |
| *C07C 255/65* | (2006.01) | |
| *B01J 27/053* | (2006.01) | |
| *B01J 27/18* | (2006.01) | |

(52) U.S. Cl.
CPC ........... *C07C 253/30* (2013.01); *B01J 27/053* (2013.01); *B01J 27/1802* (2013.01)

(58) Field of Classification Search
CPC ........................... C07C 253/30; C07C 255/65
See application file for complete search history.

(56) References Cited

U.S. PATENT DOCUMENTS

| | | | |
|---|---|---|---|
| 9,227,928 B2 | 1/2016 | Sage et al. | |
| 2013/0261041 A1* | 10/2013 | Rohwer | C11D 3/3902 252/186.25 |
| 2015/0011738 A1* | 1/2015 | Sage | C07C 253/30 534/586 |

FOREIGN PATENT DOCUMENTS

| | | |
|---|---|---|
| CX | 232350 B1 | 1/1985 |
| CX | 237123 B1 | 7/1985 |
| CX | 239407 B1 | 1/1986 |
| EP | 2821393 A1 | 1/2015 |
| EP | 3098228 A1 | 11/2016 |
| GB | 976552 | 11/1964 |
| WO | 2006067315 A1 | 6/2006 |

OTHER PUBLICATIONS

International Search Report and Written Opinion for International Application No. PCT/FR2019/050565, dated May 13, 2019, 7 pages.
Palomo et al., "Afinidad", (1985), 42(397), 4 pages (English abstract only).
Sergienko et al., "Specific structural features of molybdenum(VI) and tungsten(VI) Oxo complexes with 1-hydroxyethylidenediphosphonic acid", 1999, Crystallography Reports, vol. 44(5), pp. 877-893.

* cited by examiner

*Primary Examiner* — Joseph R Kosack
*Assistant Examiner* — Sagar Patel
(74) *Attorney, Agent, or Firm* — RatnerPrestia

(57) ABSTRACT

A process for synthesizing an azo compound by oxidation of a hydrogen compound in the presence of a catalyst and a compound of formula (I) is described in which $R_1$, $R_2$ and $R_3$ $$(R_1)(R_2)C(PO_3(R_3)_2)_2 \qquad (I)$$

are as defined. The use of a compound of formula (I) as complexing agent for a catalyst is also described.

7 Claims, No Drawings

PROCESS FOR SYNTHESIZING AZO COMPOUNDS

CROSS-REFERENCE TO RELATED APPLICATIONS

This is the national phase of International Application No. PCT/FR2019/050565, filed 14 Mar. 2019, which claims priority to French Application No. 1852264, filed 16 Mar. 2018. The disclosure of each of these applications is incorporated herein by reference in its entirety for all purposes.

The present invention relates to a process for synthesizing an azo compound, such as azobisisobutyronitrile (AZDN or AIBN), by oxidation of a hydrazo compound.

AZDN is an azo compound which is commonly used in radical polymerization processes, in particular as an initiator or catalyst. It is also known as a blowing agent for the manufacture of PVC foams or silicone seals.

Azo compounds are conventionally produced by the oxidation, with chlorine, of a hydrazo compound (WO 2006/067315). This process has also been applied to other azo compounds such as hydrazoamides (GB976552). However, this synthesis process has the major drawback, besides the intrinsic dangerous nature of chlorine, of generating hydrochloric acid as a by-product, so that the effluents cannot easily be recycled. It is apparent from this that the chlorine process is thus not suited to the current environmental constraints.

To overcome this drawback, a process has been proposed for synthesizing azo compounds using a chlorine-free oxidizing agent such as hydrogen peroxide (EP2821393). In order for the reaction to be sufficiently complete and rapid, this process requires the presence of an activating agent, generally a bromine compound such as a bromide, or else a derivative of iodine, used in an acidic medium. The reactivity of the hydrogen peroxide, and thus the yield of the reaction, are generally improved by the use of metallic catalysts in addition to the bromine or iodine compounds, in particular catalysts based on molybdenum or on tungsten (cf. CS232350 and A. PALOMO et al., "*Afinidad*", (1985), 42(397), 312-314) which have the advantage of being less toxic than tellurium, vanadium or selenium, for example.

Despite its undeniable advantages over the chlorine process, the hydrogen peroxide process however also generates effluents which are potentially harmful to the environment, specifically the residual aqueous liquors (also called aqueous mother liquors) resulting from the filtration of the reaction medium for separating AZDN therefrom. These residual aqueous liquors in fact contain a significant amount of the catalyst and the activators used. It has therefore been suggested, not just for environmental concerns but also for improving the economics of the process, to recycle these residual aqueous liquors into the reaction, possibly after concentration (cf. for example CS 239407 and CS 237123).

In addition, the synthesis process also leads to the formation of ammonium ions. However, in the presence of these ammonium ions, the catalyst has a tendency to precipitate in the form of a yellow deposit which contaminates the azo compound formed and, as a consequence, reduces the purity of said azo compound.

Moreover, the precipitation of the catalyst also causes instability of the residual aqueous liquors, thus limiting their recycling. Also, application EP2821393 proposes a process in which the addition, to the reaction medium, of a reducing agent such as hydrazine makes it possible to improve the stability of the residual aqueous liquors. However, this application does not completely solve the problems of stability of the catalyst, in particular when the residual aqueous liquors are concentrated before being recycled. Indeed, after several recycling operations, precipitation of a species containing ammonium ions is observed even though no ammonium ion has been introduced into the medium. These ammonium ions, accumulated during the process and resulting from the degradation of the nitrile functional groups of the azo derivative used, induce precipitation of the catalyst.

There is therefore a need to find a process for synthesizing azo compounds in which in particular the catalyst does not precipitate, thus leading to the synthesis of an azo compound in which the content of residual catalyst is greatly reduced and leading to a better stability of the residual aqueous liquors.

Thus, the present invention proposes to solve the problem of precipitation of the catalyst by the addition of a particular complexing agent which will be described in the description which follows. Other objectives will also become apparent in said description of the present invention.

According to a first object, the invention relates to a process for synthesizing an azo compound, said process comprising the steps of:

a) reacting an oxidizing agent with a hydrazo compound, at least one catalyst and at least one compound of formula (I):

$$(R_1)(R_2)C(PO_3(R_3)_2)_2 \quad (1)$$

wherein $R_1$ and $R_2$, which may be identical or different, are chosen independently of each other from a hydrogen atom, a saturated or unsaturated, linear, branched or cyclic, optionally substituted hydrocarbon chain, —OH and —O-alkyl, where "alkyl" represents a saturated, optionally substituted, linear or branched hydrocarbon chain comprising from 1 to 6 carbon atoms; and $R_3$ is chosen from a hydrogen atom and metal or ammonium ions;

so as to form a solution containing an azo compound;

b) recovering all or part of the reaction mixture obtained in step a);

c) separating the reaction mixture recovered into a fraction containing the azo compound and a fraction of residual aqueous liquors; and d) recovering, and optionally washing and drying, the azo compound obtained.

In the process above, the compound of formula (I) acts as a complexing agent for the catalyst and will be denoted in the rest of the patent application by the term "complexing agent".

"Optionally substituted" is understood to mean that the hydrocarbon chain and the alkyl radical may be substituted by —OH, a halogen and $N(R_4)(R_5)$, $R_4$ and $R_5$, which may be identical or different, being chosen independently of each other from a hydrogen atom, a linear or branched alkyl radical comprising from 1 to 6 carbon atoms, or else $R_4$ and $R_5$ being able to form together, and with the nitrogen atom to which they are attached, a 4-, 5-, 6- or 7-membered, preferably 5- or 6-membered, ring.

According to a preferred embodiment, within formula (I) $R_1$ is —$CH_3$ and $R_2$ is —OH.

In formula (I), $R_3$ is chosen from —H and metal or ammonium ions. Said metal ions may be chosen, in a non-limiting manner, from metals represented by columns 1 to 13 of the Periodic Table of the Elements, preferably from sodium, lithium, potassium, calcium, magnesium, aluminum, zinc, cadmium, manganese, nickel, cobalt, cerium, copper, tin, iron and chromium, more preferably from sodium, lithium, potassium, calcium, magnesium, most particularly from sodium and potassium. $R_3$ may also be chosen from ammonium ions and alkylammonium ions, in particular alkylamines, alkyleneamines and alkanolamines not containing more than two amine groups, such as ethylamine, diethylamine, propylamine, hexylamine, 2-ethylhexylamine, N-butylethanolamine and mono-, di- or triethanolamines.

Within formula (I), the radicals $R_3$ may be identical or different. According to a preferred embodiment, they are all identical, and, very particularly preferably, they are all —H.

In a preferred embodiment, the complexing agent can be chosen from alkyldiphosphonic compounds such as, for example, hydroxymethylenediphosphonic acid, 1-hydroxylethylidene-1,1-diphosphonic acid (HEDP) and 1-hydroxybutanediphosphonic acid, in their acid form or in the form of their salts. Particularly preferably, the organic complexing agent is 1-hydroxylethylidene-1,1-diphosphonic acid (HEDP), also known under the trade name Dequest® 2010.

The complexing agent may also be zoledronic acid or one of its salts (zoledronate), that is to say [1-hydroxy-1-(1H-imidazol-1-yl)ethane-1,1-diyl]diphosphonic acid or one of its salts, respectively, these being marketed by NOVARTIS under the brands Zomate®, Zomera®, Aclasta® and Reclast®.

According to an embodiment of the invention, the molar mass of the complexing agent is less than 500 g·mol$^{-1}$, preferably less than 450 g·mol$^{-1}$, more particularly less than 400 g·mol$^{-1}$.

According to another embodiment, the complexing agent is soluble in an aqueous or aqueous-organic medium, preferably in an aqueous medium, and more particularly in water.

The complexing agent may be used in a molar ratio of the complexing agent to the moles of molybdenum contributed by the catalyst of greater than 0.05:1, preferably of between 0.1:1 and 5:1, more particularly between 0.5:1 and 2:1.

The hydrazo compound oxidized during step a) of the process can be chosen from symmetrical hydrazo compounds bearing nitrogen-based functional groups, in particular nitrile or amide functional groups, such as 2,2'-hydrazo-bis-isobutyronitrile, 2,2'-hydrazo-bis-methylbutyronitrile, 1,1'-hydrazo-bis-cyclohexanecarbonitrile or 2,2'-hydrazodicarbonamide, preferably 2,2'-hydrazo-bis-isobutyronitrile.

The oxidizing agent present in step a) of the process can be of any type and can be chosen from inorganic peroxide derivatives such as for example hydrogen peroxide, potassium or sodium persulfates, potassium or sodium monohydrogen persulfates, dioxygen, water-soluble organic peroxide derivatives such as for example peracetic acid. According to a preferred embodiment, the oxidizing agent is hydrogen peroxide.

The oxidizing agent is generally introduced into the aqueous solution at a temperature of 0° C. to 40° C., preferably of 0° C. to 20° C., for a duration ranging from 2 hours to 6 hours.

The oxidizing agent is generally used in a slight molar excess relative to the hydrazo compound. The molar ratio of the oxidizing agent to the hydrazo compound is thus advantageously between 1:1 and 1.1:1, preferably between 1.01:1 and 1.05:1, limits included.

The catalyst present during step a) of the process comprises a water-soluble compound chosen from salts and acids based on a catalytic metal from columns 5 and 6 of the Periodic Table of the Elements and preferably chosen from molybdenum and tungsten, preferably molybdenum. Examples of such water-soluble compounds are in particular alkali metal or ammonium salts of molybdenum, alkali metal or ammonium salts of tungsten, phosphomolybdic acid and alkali metal or ammonium salts thereof, phosphotungstic acid and alkali metal or ammonium salts thereof, molybdosulfates and mixtures thereof. Phosphomolybdic acid and alkali metal salts thereof are preferred, in particular sodium phosphomolybdate and potassium phosphomolybdate.

The catalyst may be used in a molar ratio of the moles of metal contributed by the catalyst to the hydrazo compound which ranges for example from 0.005:1 to 0.5:1, preferably from 0.03:1 to 0.1:1.

In the process according to the invention, the complexing agent leads to a low amount of precipitation of the catalyst, or even an absence of precipitation. This is because it has been discovered, surprisingly, that the complexing agent of formula (I), by forming a complex with the catalyst, leads to an absence of precipitation of said catalyst. Another advantage of the complexing agent is that it also makes it possible for the catalyst not to lose its reactivity, which allows said catalyst to be recycled and reused in the process without having lost its effectiveness. The complexing agent/catalyst complex is removed in the residual aqueous liquors, thus enabling the entirety, or almost the entirety, of the catalyst to be recovered in the residual aqueous liquors without, however, altering the stability of said residual aqueous liquors.

According to a preferred embodiment, the solution in step a) is an acidic solution, the pH of which is preferably between 0 and 2. Thus, in order for the pH to be acidic, it is possible to add an organic or inorganic acid. Preferably, if the acid is an inorganic acid, it is chosen from hydrochloric acid, sulfuric acid, hydrobromic acid, phosphoric acid, and mixtures thereof, preferably hydrochloric acid. Preferably, if the acid is an organic acid, it is chosen from formic acid, acetic acid, and mixtures thereof. The acid may be used in a molar ratio of the acid to the hydrazo compound which ranges for example from 1:1 to 1:5.

To further improve the kinetics of the reaction and/or the reaction yield, it is advantageous to carry out oxidation step a) in the presence of an activating agent. Said activating agent can be chosen from the halogens and halides, such as for example, and in a non-limiting manner, bromine, iodine, hydrobromic and hydroiodic acids and their salts, preferably chosen from hydrobromic acid and an alkali metal bromide such as for example potassium bromide and sodium bromide. It can be used in a molar ratio of the activator to the hydrazo compound which ranges for example from 0.1:1 to 1:1, more particularly from 0.3:1 to 0.7:1.

A surfactant can optionally be added to the solution, in particular an anionic surfactant, in particular an alkyl sulfosuccinate such as di(2-ethylhexyl) sulfosuccinate.

During oxidation step a), the order of introduction of the different compounds into this solution is not critical.

At the end of this step a), an aqueous solution containing an azo compound, at least one complexing agent/catalyst complex and a quantity of oxidizing agent is obtained. Said aqueous solution may optionally comprise a quantity of an organic or inorganic acid and/or of an activating agent, and/or of a surfactant if these compounds have been added during step a).

It may be advantageous to add to the aqueous solution obtained at the end of step a) at least one reducing agent chosen from hydrazine, sodium sulfite, sodium bisulfite, and mixtures thereof. According to a preferred embodiment, and in the case where the water-soluble compound is phosphomolybdic acid, the reducing agent is hydrazine.

Hydrazine has the advantage of forming only water and gaseous nitrogen in the effluents and in the recycling loop of the process, which avoids the accumulation of salts during the recycling.

The reaction mixture thus obtained at the end of step a) is then recovered in whole or in part, for example in an amount of 30% to 60% by weight, in particular from 45% to 55% by weight, during step b) of the process according to the invention.

The reaction mixture possibly not recovered at the end of step b) may be recycled into step a), while the reaction mixture recovered is separated, in step c), into a fraction containing the azo compound and a fraction of residual aqueous liquors. During step c), the azo compound can be separated by any technique known to the person skilled in the art, preferably by filtration or centrifugation, and more particularly by centrifugation.

It may be advantageous to add to the fraction of residual aqueous liquors at least one reducing agent (even if one has already been added at the end of step a)). Said reducing agent is chosen from those already described hereinabove, and for example from hydrazine, sodium sulfite, sodium bisulfite and mixtures thereof.

According to a preferred embodiment, and in the case where the water-soluble compound is phosphomolybdic acid, the reducing agent is hydrazine. According to a preferred embodiment, the reducing agent is added at the end of step c). According to another preferred embodiment of the invention, the reducing agent is added at the end of step a) and at the end of step c).

The reducing agent is generally used in an amount necessary and sufficient for neutralizing the excess oxidizing agent measured at the end of step a) or of step c) of the process.

The fraction containing the azo compound can be washed one or more times with water, in a step d), so as to recover an azo compound having a purity of greater than 90% and two aqueous washing liquors. This high degree of purity of the azo compound is obtained in particular through the absence of precipitation of the catalyst, this absence of precipitation being linked to the presence of the complexing agent which, as described hereinabove, forms a complex with the catalyst, said complex being removed in the residual aqueous liquors.

The azo compound recovered after the separation step c) or the washing step d) may optionally undergo an additional purification step, for example, by recrystallization. This recrystallization can be carried out by any technique known to a person skilled in the art such as, for example, that described in patent application WO 2006/072699, which specifies that the recrystallization can be carried out in a solvent such as for example methylene chloride, methanol and methyl ethyl ketone. This step makes it possible to remove any possible trace of complexing agent.

In a subsequent step e) of the process, the fraction of residual aqueous liquors may be recycled in whole or in part into step a), it being understood that steps a) to e) are optionally repeated at least once, that is to say that the fraction of residual aqueous liquors may be recycled at least twice. In a variant of the process according to the invention, the fraction of residual aqueous liquors can be concentrated, in particular by distillation, before being recycled. The distillate obtained can thus be easily treated, for example incinerated, with a view to discharging it into the environment.

The process according to the invention enables, inter alia, easy treatment of the effluents with the aim of recycling them into the process and/or of treating them with the aim of discharging them into the environment. To this end, it may comprise an additional step of treating all or part of the fraction of residual aqueous liquors produced in step c) and/or of the aqueous washing liquors produced in step d) using an adsorbent, such as activated carbon, in order to retain the catalytic metal.

The process according to the invention can additionally comprise a step of recovering the catalytic metal in the form of an aqueous solution, by treating the adsorbent with the aid of a basic aqueous solution, in particular of sodium hydroxide. The preference in industry is to pass the fraction of residual aqueous liquors and/or of the aqueous washing liquors to be treated through a column containing the adsorbent, for example in granulated form, then to recover the catalytic metal by passing a basic solution through this column, according to the well-known techniques for using these adsorbents.

The aqueous solution of catalytic metal can thus be recycled into step a) of the process, optionally after concentration, while the residual aqueous liquors resulting from the filtration of the adsorbent and/or the aqueous liquors from washing the absorbent can be discharged into the environment. This makes it possible to recover and recycle an effective amount of catalyst while discharging an effluent containing very little catalyst into the environment.

The process according to the invention thus makes it possible to obtain within a reasonable time an increased particle size of the azo compounds produced, typically close to 150 μm (as measured by laser diffraction), which may prove advantageous in certain applications.

Thus, the process of the present invention is most particularly advantageous when the residual aqueous liquors and/or the catalyst and/or the activator agent, and in particular the residual aqueous liquors and/or all of the components of the catalytic system, are recycled. These recycling operations have, among others, the great advantage of not discharging into the effluents the catalytic system and in particular the metal salts which are expensive but also and above all harmful to the environment.

A subject of the invention is also the use of a compound of formula (I) as has been defined above as a complexing agent. According to one embodiment, said compound of formula (I) is used as a complexing agent for a catalyst, preferably in a process for synthesizing an azo compound. According to one embodiment, said compound of formula (I) is used as a complexing agent in a process for synthesizing an azo compound. Said compound of formula (I) is preferably used as a complexing agent for a catalyst, for example for a catalyst as defined hereinabove, in a process for synthesizing an azo compound comprising a step of reacting an oxidizing agent with a hydrazo compound, at least one catalyst and at least said compound of formula (I) so as to form a solution containing an azo compound. Said compound of formula (I) is preferably used as a complexing agent for a catalyst, for example for a catalyst as defined hereinabove, in a process for synthesizing an azo compound, for example in the process as defined hereinabove.

A third subject of the invention is the residual aqueous liquors comprising the complexing agent/catalyst complex described above, said residual aqueous liquors being obtained during the process for synthesizing an azo compound according to the invention.

The invention will be better understood in light of the following examples, which are given purely by way of illustration and in no way limit the scope of the invention.

EXAMPLES

In the examples which follow:

DHC denotes hydrazobisisobutyronitrile, a hydrazo compound obtained industrially by reaction of acetone cyanohydrin with hydrazine hydrate, filtration and then washing with water, and stored in a refrigerator (T<10° C.). Its moisture content is 12.7% and its purity is greater than 99% by analysis.

the phosphomolybdic acid used is a product sold by Aldrich which corresponds to the formula $H_3[P(Mo_3O_{10})_4] \cdot xH_2O$ and is used as is (molar mass 1825.25 g/mol in anhydrous form). The product used has a molybdenum content of 50%.

DOSS denotes di(2-ethylhexyl) sulfosuccinate.

AZDN (or AIBN) denotes azobisisobutyronitrile.

Method for Sampling and Assaying the Content of Residual Peroxide

In the following examples the contents of residual peroxide are measured as follows.

About 3 ml to 5 ml of the reaction medium in suspension is withdrawn and is filtered in order to remove DHC and solid AZDN present. About exactly 1 gram of the filtered solution is weighed out and introduced into a 250 ml flask, and to this are added 50 ml of distilled water, 15 ml of 30% by weight sulfuric acid and 15 ml of a 30% KI solution. The flask is stoppered and left in the dark for 15 min. It is then titrated with a solution of sodium thiosulfate having a normality of 0.1 N until the yellow coloration disappears. The content of residual hydrogen peroxide ($H_2O_2$) is calculated as follows:

$$\% \; H_2O_2 \; \text{résiduel} = \frac{\text{Volume de thiosulfate de sodium 0.1 N (en mL)}}{2 \times 100 \times \text{masse de filtrat (en grammes)}}$$

The assaying of the residual molybdenum is carried out by the optical ICP (or inductively coupled plasma) technique. The particle size measurement is carried out using a Mastersizer® S device. The measurement is performed on wet crystals using as dispersant water and a drop of Igepal® (ethoxylated nonylphenol) surfactant, after 10 minutes of circulation in the measurement cell.

Example 1: Complexing Agent Test

A mixture is prepared containing 100 ml of a 5% by mass aqueous hydrogen bromide solution, 1.5 g of Phosphomolybdic acid (catalyst) and 1 g of complexing agent.

After 30 minutes, a first observation is made on the solubility of the Phosphomolybdic acid in the absence of ammonium bromide ($NH_4Br$).

10 ml of a 37.5% aqueous ammonium bromide solution is then added. After 30 minutes, a second observation is made on the solubility of the phosphomolybdic acid in the presence of ammonium bromide.

The results are collated in table 1 below:

TABLE 1

| Complexing agent | Presence of precipitate (without $NH_4Br$) | Presence of precipitate (with $NH_4Br$) |
|---|---|---|
| 1-Hydroxyethylidene-1,1-diphosphonic acid (Dequest ® 2010) | NO | NO |
| Aminotris(methylenephosphonic acid) (Dequest ® 2000) | YES | YES |
| Diethylenetriaminepenta(methylene-phosphonic acid) (Dequest ® 2060) | YES | YES |
| 2,2'-Ethylenebis(nitrilomethylidene)diphenol N,N'-ethylenebis(salicylimine) (Salen) | YES | YES |
| Glycerol | NO | YES |
| 2-Amino-3-(1H-imidazol-4-yl)propanoic acid (DL Histidine) | YES | YES |
| 2-Amino-3-mercaptopropanoic acid (DL Cysteine) | NO | YES |
| Methionine | NO | YES |
| 1,10-Phenanthroline | YES | YES |
| Blank | NO | YES |

The tests show that the compounds other than those corresponding to formula (I) do not make it possible to prevent the appearance of a precipitate in the presence of ammonium ions. On the other hand, when the complexing agent corresponds to the definition of formula (I), no precipitate is observed. This absence of precipitate reflects the stability of the phosphomolybdic acid in the presence of the complexing agent in a medium containing ammonium ions. The complexing agent of formula (I), for example Dequest® 2010, makes it possible to prevent the precipitation of the phosphomolybdic acid in the presence of ammonium ions.

Another test, performed under the same operating conditions as above, was carried out in order to determine the amount of compound of formula (I) which is sufficient to prevent the precipitation of the phosphomolybdic acid in the presence of $NH_4Br$ the amount of complexing agent of formula (I) was gradually reduced until the formation of a precipitate was observed.

This series of tests made it possible to demonstrate that, in a solution comprising containing 100 ml of a 5% by mass aqueous hydrogen bromide solution, 1.5 g of phosphomolybdic acid (catalyst) and 5 ml of a 37.5% by mass $NH_4Br$ solution, an amount of 0.35 g of complexing agent of formula (I), such as Dequest® 2010, is sufficient for inhibiting the precipitation of the phosphomolybdic acid, i.e. a complexing agent/phosphomolybdic acid molar ratio of 0.2.

Example 2: Counter Example (Process in the Absence of Complexing Agent)

126 g of AZDN (0.77 mol), 128 g of DHC (hydrazobisisobutyronitrile) (0.77 mol), an aqueous solution composed of 635 g of water, 35 g of HBr, 7 g of phosphomolybdic acid (50% Mo content, i.e. 0.036 mol of molybdenum), and 0.1 g of DOSS (di(2-ethylhexyl) sulfosuccinate) are introduced into a 1.5 l capacity reactor equipped with a stirring system allowing the mixing of a suspension. After starting the stirring and the jacketed cooling system, stabilization of the temperature at around 10° C. is awaited.

Once a temperature of 10° C. has been reached, 78.05 g of 35% $H_2O_2$ (i.e. 0.80 mol of $H_2O_2$) are introduced continuously over 4 h. During the reaction, the medium is maintained at a temperature of between 10° C. and 12° C. The reaction is stopped about 20 to 30 minutes after having introduced the entire amount of $H_2O_2$. The end of the reaction is made visible by the formation of bromine and by the increase in the redox potential (before the introduction of $H_2O_2$ the potential is about 400 mV and at the end of the reaction, that is to say after the introduction of the entirety of the $H_2O_2$, the potential is about 800 mV). The redox potential is measured using a platinum redox probe.

The suspension from the reactor is then completely filtered. 290 g of crude AZDN containing 15% moisture is obtained, i.e. a yield of 95%. In addition, 20 ml of water are also used to rinse the filter and are added to the residual aqueous liquors.

The obtained residual aqueous filtration liquors, i.e. 740 g, are neutralized by hydrazine hydrate in order to remove the peroxide excess and the bromine formed (assaying found 0.1% of residual $H_2O_2$ equivalent). The redox electrode is utilized to bring the potential back to its initial value, i.e. about 300 mV to 400 mV.

Half of the residual aqueous liquors, i.e. 374 g, is put aside to be reused directly in the following test, whereas the other half undergoes a step of concentration under vacuum aiming to remove about 60% to 65% of the water from this fraction of residual aqueous liquors. This is carried out under a vacuum of 250 millibar (25 kPa) between 55° C. and 60° C. For 325 g of residual aqueous liquors employed, 235 g of an aqueous distillate fraction and 90 g of resulting concentrated solution are thus obtained. This resulting concentrated fraction, containing the catalytic system, may thus be reused with the fraction of untreated residual aqueous liquors for the following cycle.

Half of the AZDN obtained is washed four times with water using 200 ml of water each time. The other half of the crude AZDN is kept as is (with the fraction of residual aqueous mother liquors present in the crystals) to be recycled during the following cycle in the following example.

Thus, practically all of the components of the catalytic system are recycled, except for the fraction which is inherent to the losses in transfer and sampling for assays and also the fraction of residual aqueous liquors retained in the crystals of the washed AZDN produced.

Example 3: Counterexample (Process without Complexing Agent and with Recycling)

145 g of the crude unwashed AZDN obtained previously (i.e. 0.78 mol of AZDN containing about 15 g of residual aqueous liquors in the crystals), 128 g of DHC (hydrazobisisobutyronitrile) (0.78 mol), 0.05 g of DOSS (di(2-ethylhexyl) sulfosuccinate), 374 g of residual aqueous liquors resulting from the filtration of the reaction medium during the previous test and also the residual aqueous liquors concentrated during the previous test are introduced into the reactor of the previous example. The bromides present in the recycled fractions of residual aqueous liquors are assayed in order to determine the supplement of catalytic system required. In order to maintain a reaction medium of the same composition as that of the previous example, 4 g of HBr, 0.78 g of phosphomolybdic acid and 150 g of water are typically added, this feedstock of water being calculated according to the water contents of the reactants used (aqueous HBr solution, moisture content of the DHC) in order to return to the initial composition of the previous test.

This water, 150 g, will make it possible, in an industrial process, to more easily feed the solid DHC in the form of an aqueous suspension from a holding tank, for example.

The reaction is then conducted as in the previous example by continuously pouring 78.05 g of 35% $H_2O_2$ over a period of 4 hours into the reaction medium maintained between 10° C. and 12° C.

The process is thus carried out by recycling into test n+1 half of the AZDN and of the residual aqueous liquors obtained and concentrating the other half of the residual aqueous liquors in test n.

The three first recycling operations lead to the obtaining of white products with a purity of greater than 95% by NMR analysis. During the fourth recycling operation the formation of a significant deposit with a yellow color is noted. This deposit contaminates the AZDN obtained, washing operations with water do not make it possible to remove this deposit.

It is also noted that the deposit forms again over time in the residual aqueous liquors obtained after filtration.

The following concentration step was conducted on these residual aqueous liquors, after filtration to remove these crystals. At the end of the concentration, it is noted that these crystals have reformed at the bottom of the boiler and hence contaminate the concentrated solution of the residual aqueous liquors.

Analysis of this deposit, by X-ray fluorescence and X-ray diffraction, shows that it is a crystalline compound of ammonium phosphomolybdate, these compounds being known for being very insoluble in acidic media.

The formation of ammonium ions in the medium seems to be attributable to the hydrolysis of the cyano by-products. The ammonium ions thus accumulate over the course of the operations of recycling into the reaction medium, causing the precipitation of the catalyst.

Example 4: Process in the Presence of Dequest® 2010 (According to the Invention)

The process of the invention is carried out according to the same procedure as that described in counterexample 2, but with addition of 20.7 g of a 60% aqueous solution of Dequest® 2010 (i.e. 1.65 mol of Dequest® 2010 per mole of molybdenum) to the reaction medium before the introduction of the hydrogen peroxide solution.

A series of recycling operations is carried out as described in counterexample 3. In this example, 12 recycling operations are thus carried out, without noting formation of precipitate contaminating the AZDN obtained or precipitating in the aqueous mother liquors or during the concentration operations.

The supplements of catalytic system are carried out throughout the process as indicated in counterexample 3, but in this example, for an addition of 4 g of HBr; 1.4 g of Dequest® 2010 (i.e: 2.35 g of 60% aqueous solution of Dequest® 2010) are also added.

On the twelfth recycling operation, the yields of washed AZDN remain above 95%, the residual bromide content of the washed AZDN is from 80 ppm to 90 ppm and the purity by NMR analysis is greater than 98%. The particle size remains constant and is between 110 μm and 130 μm (number-average diameter).

Example 5: Recrystallization of the AZDN Obtained by the Process

The AZDN obtained according to example 4 at the end of the twelfth recycling operation is washed 3 times with 200 ml of water and then dried at ambient temperature (residual moisture content 1% to 2% by weight). 20 g of this AZDN are then dissolved in 250 ml of methanol at 35° C. When the crystals have dissolved, the temperature is lowered to 2° C. to recrystallize the AZDN. The mixture is then filtered under cold conditions; the methanol solvent fraction recovered is put aside to be reused in the next recrystallization. The AZDN crystals recovered on the filter are washed with a 50 ml portion of water and then dried.

The operation is started again by once more taking 20 g of the AZDN obtained at the end of the twelfth recycling operation and using the methanol fraction previously recovered, and possibly supplementing it to compensate for losses of solvent or to completely dissolve the 20 g of AZDN employed.

Five successive recrystallization operations were thus carried out each time re-employing the fraction of recovered methanol. The search for traces of molybdenum by the optical ICP method on an ICAP 6500 spectrometer device shows that all of the AZDN thus obtained is free of traces of residual molybdenum (detection limit of 1 ppm).

The invention claimed is:

1. A process for synthesizing an azo compound, the process comprising the steps of:
   a) reacting an oxidizing agent with a hydrazo compound, at least one catalyst comprising a water-soluble compound chosen from alkali metal or ammonium salts of molybdenum, alkali metal or ammonium salts of tungsten, phosphomolybdic acid and alkali metal or ammonium salts thereof, phosphotungstic acid, alkali metal or ammonium salts thereof, molybdosulfates and mixtures thereof, and at least one compound of formula (I):

   $$(R_1)(R_2)C(PO_3(R_3)_2)_2 \quad\quad (I)$$

so as to form a solution containing an azo compound, wherein:

$R_1$ and $R_2$, which may be identical or different, are chosen independently of each other from a hydrogen atom, a saturated or unsaturated, linear, branched or cyclic, optionally substituted hydrocarbon chain, —OH and —O-alkyl, where "alkyl" represents a saturated, optionally substituted, linear or branched hydrocarbon chain comprising from 1 to 6 carbon atoms; and $R_3$ is chosen from a hydrogen atom and metal or ammonium ions;
   b) recovering all or part of the reaction mixture obtained in step a);
   c) separating the reaction mixture recovered into a fraction containing the azo compound and a fraction of residual aqueous liquors; and
   d) recovering, and optionally washing and drying, the azo compound obtained.

2. The process as claimed in claim 1, wherein the compound of formula (I) is chosen from [1-hydroxy-1-(H-imidazol-1-yl)ethane-1,1-diyl]diphosphonic acid or one of its salts, hydroxymethylenediphosphonic acid, 1-hydroxylethylidene-1,1-diphosphonic acid (HEDP) and 1-hydroxybutanediphosphonic acid, in their acid form or in the form of their salts.

3. The process as claimed in claim 1, wherein the hydrazo compound is chosen from symmetrical hydrazo compounds bearing nitrogen-based functional groups.

4. The process as claimed in claim 1, wherein the oxidizing agent is chosen from inorganic peroxide derivatives.

5. The process as claimed in claim 1, wherein at least one reducing agent is added to the aqueous solution obtained in step a).

6. The process as claimed in claim 1, wherein at least one reducing agent is added to the fraction of residual aqueous liquors.

7. The process as claimed in claim 5, wherein the reducing agent is chosen from hydrazine, sodium sulfite, sodium bisulfite and mixtures thereof.

* * * * *